US007169965B2

(12) United States Patent
Iimura et al.

(10) Patent No.: US 7,169,965 B2
(45) Date of Patent: Jan. 30, 2007

(54) TRANSGENIC PLANTS EXPRESSING SECRETORY LACCASE AND USE THEREOF

(75) Inventors: Yosuke Iimura, Ibaraki (JP); Yoshihiro Katayama, Tokyo (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 235 days.

(21) Appl. No.: 10/263,819

(22) Filed: Oct. 4, 2002

(65) Prior Publication Data

US 2003/0097681 A1    May 22, 2003

(30) Foreign Application Priority Data

Oct. 5, 2001    (JP)    ............................. 2001-309824

(51) Int. Cl.
*C12N 15/09* (2006.01)
*C12N 15/82* (2006.01)
*C12N 15/31* (2006.01)
*A01H 5/00* (2006.01)

(52) U.S. Cl. ...................... 800/278; 800/298; 800/288; 435/69.1; 435/468

(58) Field of Classification Search ............... 536/23.7; 435/69.1, 468, 320.1; 800/278, 298, 288
See application file for complete search history.

(56) References Cited

U.S. PATENT DOCUMENTS 6,642,439 B2*    11/2003    Iimura et al. ............... 800/288

FOREIGN PATENT DOCUMENTS

| EP | 0 223 452 A2 | 5/1987 |
|---|---|---|
| JP | 06-125782 | 5/1994 |
| JP | 08-051986 | 2/1996 |
| JP | 09-056378 | 3/1997 |
| JP | 09-503126 | 3/1997 |
| JP | 09-505481 | 6/1997 |
| JP | 2000-342275 | 12/2000 |
| JP | 2001-232345 | 8/2001 |
| WO | WO 95/07988 | 3/1995 |
| WO | WO 95/15390 | 6/1995 |
| WO | WO 00/20615 | 4/2000 |

OTHER PUBLICATIONS

Ong. Gene, vol. 196, pp. 113-119, 1997.*
Becker et al. Ann. Proc. Cytochem Soc. Of Europe, pp. 325-331, 1993.*
Giardina, P., et al., Cloning and Sequencing of a Laccase Gene from the Lignin-Degrading Basidiomycete *Pleurotus ostreatus*, Applied and Environmental Microbiology, vol. 61, pp. 2408-2413 (1995).
Hatamoto, O., et al., Cloning and Expression of a cDNA Encoding the Laccase from *Schizophyllum commune*, Biosci. Biotechnol. Biochem., vol. 63, pp. 58-64 (1999).
Iimura, Y., et al., Degradation and Solubilization of $^{13}$C-, $^{14}$C-side Chain Labeled Synthetic Lignin (Dehydrogenative Polymerizate) by Laccase III of *Coriolus versicolor*, Biosci. Biotech. Biochem., vol. 59, pp. 903-905 (1995).
Lang, E., et al., Production of ligninolytic enzymes by *Pleurotus* sp. and *Dichomitus squalens* in soil and lignocellulose substrate as influenced by soil microorganisms, FEMS Microbiology Letters, vol. 167, pp. 239-244 (1998).
Mikuni, J. and Iimura, Y., Coriolus versicolor CVL3 Gene for Laccase, EMBL database, Abstract (1992).
EPO Search Report, (Feb. 6, 2003).
G. Amitai, et al., Oxidative biodegradation of phosphorothiolates by fungal laccase, FEBS Letters, vol. 438, pp. 195-200 (1998).
T. Asano, et al., Expression in tobacco plant of *hadA* and *hadB* genes involved in 2,4,6-tri-chlorophenol degradation by *Burkholderia pickettii*, Abstract 2D1p22, Japan Society for Bioscience, Biotechnology, and Agrochemistry, Abstracts for the Annual Meeting, vol. 72 (1998) and English translation.
R.M. Berka, et al., Characterization of the Gene Encoding an Extracellular Laccase of *Myceliophthora thermophila* and Analysis of the Recombinant Enzyme Expressed in *Aspergillus oryzae*, Applied and Environmental Microbiology, vol. 63, No. 8, pp. 3151-3157 (1997).
J.-M. Bollag, et al., Laccase-Mediated Detoxification of Phenolic Compounds, Applied and Environmental Microbiology, vol. 54, No. 12, pp. 3086-3091 (1988).
M. Chivukula & V. Renganathan, Phenolic Azo Dye Oxidation by Laccase from *Pyricularia oryzae*, Applied and Environmental Microbiology, vol. 61, No. 12, pp. 4374-4377 (1995).
T. Hoff, et al., Transformation of Halogen-, Alkyl-, and Alkoxy-Substituted Anilines by a Laccase of *Trametes versicolor*, Applied and Environmental Microbiology, vol. 49, No. 5, pp. 1040-1045 (1985).
C. Johannes, et al., Degradation of anthracene by laccase of *Trametes versicolor* in the presence of different mediator compounds, Appl. Microbiol. Biotechnol., vol. 46, pp. 313-317 (1996).
Y. Nagata, et al., Production of transgenic plant having *Sphingomonas paucimobilis* UT26-derived y-HCH dehydrochlorinase gene (*linA*), Abstract 3Ap6, Japan Society for Bioscience, Biotechnology, and Agrochemistry, Abstracts for the Annual Meeting, vol. 71, p. 89 (1997) and English translation.
A. Ricotta, et al., Role of a Laccase in the Degradation of Pentachlorophenol, Bull. Environ. Contam. Toxicol., vol. 57, pp. 560-567 (1996).

(Continued)

*Primary Examiner*—Medina A. Ibrahim
(74) *Attorney, Agent, or Firm*—Finnegan, Henderson, Farabow, Garrett & Dunner, L.L.P.

(57) ABSTRACT

A transformed plant expressing a DNA encoding secretory laccase from Coriolus versicolor, and a method of producing laccase are disclosed. Also disclosed is a method of decomposing and/or removing hazardous chemical substances by cultivating the transformed plant in an environment contaminated with the hazardous chemical substances.

9 Claims, 2 Drawing Sheets

OTHER PUBLICATIONS

L. Roy-Arcand & F.S. Archibald, Direct dechlorination of chlorophenolic compounds by laccases from *Trametes* (*Coriolus*) *versicolor*, Enzyme Microb. Technol., vol. 13, pp. 194-203 (1991).

D.S. Yaver, et al., Purification, Characterization, Molecular Cloning, and Expression of Two Laccase Genes from the White Rot Basidiomyete *Trametes villosa*, Applied and Environmental Microbiology, vol. 62, No. 3, pp. 834-841 (1996).

English translation of the abstract of JP 2001-232345, published Aug. 28, 2001.

Richardson, A.E. et al., "Extracellular secretion of *Aspergillus* phytase from *Arabidopsis* roots enables plants to obtain phosphorus from phytate," Plant J. 25(6):641-649 (2001).

Taisei Corporation Institute of Technology Reports 33:67-70 (2000).

Japan Society on Water Environment Annual Meeting Abstracts, 29:153 (1995).

Jünsson, L.J. et al., "Laccase from the white-rot fungus *Trametes versicolor*: cDNA cloning of *lcc1* and expression in *Pichia pastoris*," Curr. Genet. 32:425-430 (1997).

* cited by examiner

TRANSGENIC PLANTS EXPRESSING SECRETORY LACCASE AND USE THEREOF

This application claims the right to priority based on Japanese Application No. 2001-309824, filed Oct. 5, 2001.

BACKGROUND OF THE INVENTION

1. Field of the Invention

The present invention relates to a plant in which a phenoloxidase gene is introduced, a method of producing phenoloxidase using the plant, and a method of decomposing and removing hazardous chemical substances using the plant.

2. Description of the Related Art

Phenoloxidase is an enzyme which converts phenols to o-quinone or p-quinone by oxidization, and laccase is a representative example. Laccase is widely present in animals and plants, and fungi, and in recent years laccase could be obtained as an extracellular enzyme of a microbial cell having the ability to produce laccase. Laccase as an extracellular enzyme is produced and purified by purifying a culture filtrate of cells capable of producing the enzyme, or by conducting genetic recombination of laccase genes into hosts e.g. fungi such as Aspergillus genus, culture of the transformant in a liquid medium, and collection of laccase from the culture solution (YAVER, D. S. et al. (1996) Appl. Environ. Microbiol. 62: 834–841, Berka, R. M. et al. (1997) Appl. Environ. Microbiol. 63: 3151–3157). However, in producing laccase using microorganisms capable of producing laccase, particularly the above recombinant, the production efficiency is enhanced, but in the meantime a problem arises that culture and purification etc. are costly. Therefore, although there have been many reports on the usefulness of laccase in wastewater treatment (e.g. coagulative precipitation treatment of organochlorine compounds in pulp bleaching drainage), decomposition of hazardous chemical substances (e.g. decomposition of chlorinated phenols) (Roy-Arcand, L and Archibald, F. S. (1991) Enzyme Microbial Technol. 13: 194–203, Ricotta, A. et al. (1996) Bull Environ. Contam. Toxicol. 57: 560–567, Johannes, C. et al. (1996) Appl. Microbiol Biotechnol. 46: 313–317, Hoff, T. H. O. M. et al. (1985) Appl. Environ. Microbiol. 49: 1040–1045, Chivukula, M. U. R. A. and Renganathhan, V. (1995) Appl. Environ. Microbiol. 61: 4374–4377, Bollag J. -M. et al. (1988) Appl. Environ. Microbiol. 54: 3086–3091, Amitai, G. et al. (1998) FEBS Lett 438: 195–200), production of artificial lacquer paints, turbidity prevention for beverages, clinical analysis, etc., in fact, laccase has not come into practical use. Thus, laccase is brought to a commercial stage only for washing and decoloring denim, which is considered to have high added value.

Accordingly, there is a demand in many fields for a simple production method of phenoloxidase, in particular laccase, which has high production efficiency and desirable cost performance. Though there have been confirmed many patent applications or documents on production methods of phenoloxidase, e.g. laccase (Japanese Patent Application Laid-Open (kokai) No. 9–56378, Japanese Patent Application Laid-Open (kohyo) No. 9–503126, Japanese Patent Application Laid-Open (kohyo) No. 9–505481, YAVER, D. S. et al. (1996) Appl. Environ. Micorbiol. 62: 834–841, Berka, R. M. et al. (1997) Appl. Environ. Microbiol. 63: 3151–3157, etc.), a method which is satisfactory from a practical point of view has not yet been found.

On the other hand, physicochemical treatments are under development as treatment technologies for cases wherein hazardous chemical substances such as PCB, BHC and DDT which are produced as industrial chemical substances, or dioxins which are unintentional products, are stocked at high concentrations or accumulated in an environment. For example, photochemical decomposition, supercritical decomposition, solvent extraction decomposition, catalytic oxidization, vapor phase hydrogenation reduction, melt combustion, heat treatment in reducing atmosphere and glassification treatment are under validation testing. However, these physicochemical methods are not practical, from a viewpoint of cost-effectiveness, for hazardous chemical substances accumulated at low levels in an environment such as in the soil or in rivers, and moreover in situ treatment methods for these substances are required. These hazardous chemical substances diffused over a wide area, even though their concentrations are low, have sufficient concentration levels for endocrine disruption. As a means to overcome this problem, bio-remediation has been conducted with the use of microorganisms that strongly decompose hazardous chemical substances, but such a decontamination method by microorganisms still has drawbacks. That is, the inoculation of the microorganisms and application of nutrient sources needs to be conducted in order to maintain dominance of such microorganisms over a long period, and this becomes more difficult as the contaminated area expands.

From this perspective, in recent years, attempts at decontamination have been made by phyto-remediation (restoration of the environment by plants) which utilizes plants. Plants can be grown independently taking nourishment from the sun, water, and inorganic ions, and can be cultivated extensively by controlling their seeds. Because of this, they have attracted attention as a sustainable environmental decontamination method.

The phyto-remediation that has been examined includes use of detoxification mechanisms or transpiration ability which plants inherently possess. Further, attempts to strengthen the environmental decontamination function of plants have recently made by introducing microorganism-derived genes. However, environmental remediation by transformant plants that has been examined so far involves, in the case of, for example, agricultural chemicals, heavy metals, or the like, transportation and accumulation of these substances to and in cell fractions. Therefore, when the plants die, the accumulated environmental contaminants are released again into the environment and thus this does not lead to a fundamental solution for decontamination. Furthermore, in the case where the hazardous chemical substances are dioxins or PCB, it is predictable that readily degradable substances are decomposed while difficult-to-degrade and highly toxic substances are condensed and accumulated. Thus, there is no other choice to consider that conventional phytoremediation is insufficient.

Against this background, attempts to decompose hazardous chemical substances directly in plant cells using transformant plants into which an enzyme gene for decomposing hazardous chemical substance derived from microorganism are introduced, have been made with respect to 2,4,6-trichlorophenol (Japan Society for Bioscience, Biotechnology, and Agrochemistry, Abstracts for the Annual Meeting, p164, 1998) or γ-hexacyclohexane (Japan Society for Bioscience, Biotechnology, and Agrochemistry, Abstracts for the Annual Meeting, p89, 1997).

Incidentally, it has been clarified that laccase can decompose various chemical substances which are not readily degradable. Laccase can oxidatively decompose endocrine disrupting chemicals including chlorophenols, agricultural chemicals, polycyclic aroma hydrocarbons, alkyl phenol, aroma hydrocarbons, and nitro compounds.

Accordingly, when genes for phenoloxidase, e.g. laccase, are incorporated and plants which can express a function of the genes are prepared, a method of producing phenoloxidase at high yields and desirable cost levels can be established. Also, it is further possible to accomplish phytoremediation which is useful for decomposing and removing hazardous chemical substances in the environment.

Although there have already been reports (Japanese Patent Application Laid-Open (kokai) Nos. 6-125782, 8-051986, etc.) on methods for obtaining transformant plants by introducing various foreign genes into plants, it is difficult to introduce active phenoloxidase into plants and enable stable secretion and production of the protein locally from roots thereof. Until now there have been no reports on preparation of such transformant plants, methods of producing phenoloxidase by such plants, and phyto-remediation utilizing such plants.

SUMMARY OF THE INVENTION

Under the above mentioned technical background, it is an object of the present invention to provide a plant which can secrete and produce phenoloxidase (hereinafter referred to as "protein of the present invention") e.g. laccase etc. from a root thereof, and a method of decomposing and removing hazardous chemical substances using the plant.

The present inventors have intensively made studies in order to solve the above problems. As a result, they have found that a plant into which a gene for phenoloxidase, e.g. laccase, is introduced can secrete and produce the enzyme from a root thereof and such plant enables decomposition and removal of hazardous chemical substances, thereby completing the present invention.

Namely, the present invention provides the following (1) to (10):

(1) A plant into which a DNA encoding phenoloxidase is introduced, the DNA being expressed therein.
(2) The plant according to (1), wherein the DNA is locally expressed in a root thereof.
(3) The plant according to (1) or (2), wherein the DNA encoding phenoloxidase is a DNA encoding laccase.
(4) The plant according to (3), wherein the laccase is a secretory laccase.
(5) The plant according to (3), wherein the laccase is derived from basidiomycete.
(6) The plant according to (5), wherein the basidiomycete belongs to the genus
(7) A plant into which a DNA encoding the following protein (a) or (b) is introduced, the DNA being expressed therein:
(a) a protein having an amino acid sequence shown in SEQ ID NO:2; or
(b) a protein having an amino acid sequence comprising deletion, substitution, or addition of one or several amino acids relative to the amino acid sequence shown in SEQ ID NO:2, and which has laccase activity.
(8) The plant according to any of (1) to (7), wherein the plant is a seed plant.
(9) A method of producing phenoloxidase, comprising the steps of:
culturing the plant described in any one of (1) to (8) in a water culture solution; and
collecting phenoloxidase from the culture solution.
(10) A method of decomposing and removing hazardous chemical substances, comprising the step of:

cultivating the plant according to any one of (1) to (8) in an environment contaminated with a hazardous chemical substance.

DESCRIPTION OF SEQUENCE LISTING

Figure 1:
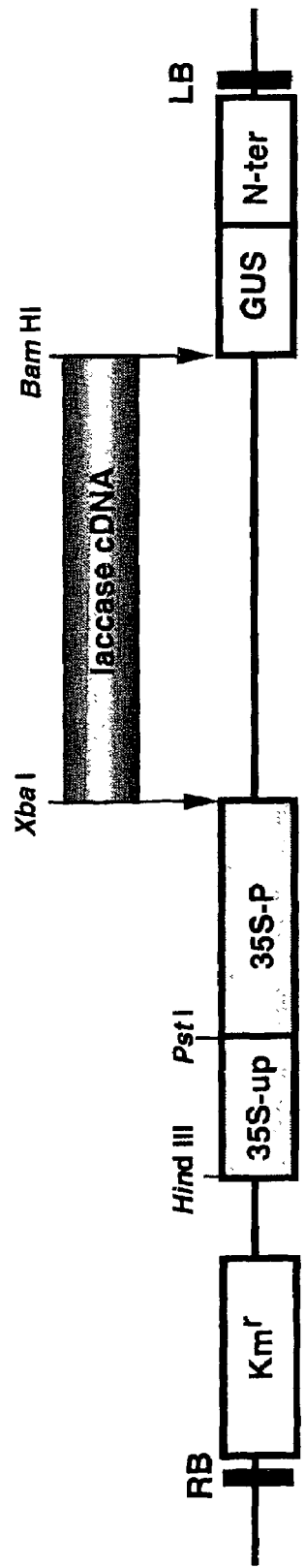
FIG. 1 shows a structure of plasmid pW35Sflac/pBI121.

SEQ ID NO:3 is Primer LfXb.
SEQ ID NO:4 is Primer LBa.
This specification includes the contents as disclosed in the specification and/or drawings of Japanese Patent Application No. 2001-309824, which is a priority document of the present application.

DESCRIPTION OF THE PREFERRED EMBODIMENTS

Hereinafter, the present invention will be described in detail.

A plant of the present invention is a plant in which DNA encoding phenoloxidase is introduced, wherein the DNA is expressed therein. Phenoloxidase is an enzyme which oxidizes phenols thereby to convert them to o-quinone or p-quinone in the presence of oxygen. It includes monophenol oxidization enzymes such as tyrosinase, which act on not only polyphenols but also monophenols, and diphenol oxidization enzymes such as laccase, which act on only p-diphenols.

Among these, laccase is particularly preferable in terms of variety of applications, enzyme activity, ability to decompose and remove hazardous chemical substances, etc.

Laccase is present naturally and widely in animals, plants, and fungi. Though laccase from any source can be used for the present invention, laccase from various microorganism, e.g. basidiomycetes, ascomycetes, and hyphomycetes is preferable particularly in terms of operational ease in enzyme production (stability of enzyme, ability to reduce toxicity of hazardous chemical substances) etc. Among these, laccase obtained from basidiomycetes is particularly preferable. Examples of basidiomycetes include the microorganisms which belong to the genus *Coriolus, Schizophyllum* or *Pleurotus*, for example, *Coriolus versicolor, Schizophyllum commune*, and *Pleurotus ostreatus*.

Further, laccase which can be introduced into the plant of the present invention may be a secretory laccase. Herein, the phrase "secretory laccase" means laccase which is secreted outside of plant bodies via a signal sequence that is necessary to secrete proteins outside of plant bodies.

As the proteins of the present invention which can be introduced into plants, a protein having an amino acid sequence of SEQ ID NO:2 may be given. Further, the proteins of the present invention include not only a natural protein, having laccase activity, obtained from basidiomycete, but also a protein which may comprise substitution, deletion or addition of one or several amino acids relative to the natural protein as long as the protein does not lose the activity. In this sequence, a region comprising a peptide represented by the amino acid sequence of amino acid positions 1 to 21, functions as a signal sequence, and this signal sequence allows the protein of the present invention to stably and reliably be secreted outside of plant bodies. The signal sequence is a gene for secreting the protein and is functionally linked with N-terminus of laccase gene. Therefore, when it is desired to obtain from a transformant plant a secretory protein e.g. secretory laccase, it is preferable to avoid substitutions, deletions, and additions in the amino acid sequence of amino acid positions 1 to 21 in the amino acid sequence shown in SEQ ID NO:2.

Secretion and production can also be achieved by linking with phenoloxidase a known signal sequence, other than the signal sequence naturally existing in the laccase gene, which is represented by the amino acid sequence of the above amino acid positions 1 to 21. However, it is particularly preferable to employ the secretory laccase having the amino acid sequence, which comprises the signal sequence shown in SEQ ID NO:2, because it is possible to stably and reliably secrete laccase outside of plant bodies.

In order to isolate the DNA encoding the protein of the present invention which can be introduced into plants, gene cloning methods can be used. For example, there is a method wherein an enzyme is purified, an amino acid sequence is determined, and synthetic nucleotides are prepared based on the sequence to select the DNA from a gene library by hybridization. Moreover, there is also a method wherein primers used for PCR (Polymerase Chain Reaction) are prepared based on the known gene nucleotide sequence information without purifying the enzyme, to amplify and isolate a specific region or whole region of the gene by performing PCR.

The DNA encoding the protein of the present invention which can be introduced into plants, can be expressed by introducing it into plants with a suitable promoter or the like. The promoter includes a promoter which enables local expression. For example, cauliflower mosaic virus 35S promoter (CMV 35S-P) which enables strong expression in roots may be used. Further, in addition to this, known promoters which promote local expression in leaves or stems can be used, but operations for separation and purification of the proteins produced therefrom are complicated. Accordingly, it is particularly preferable to use a promoter which enables strong expression in roots. It is noted herein that the phrase "local expression" means not only expression occurring only in a particular local part of a plant but also local expression where an expression in a particular part is much stronger compared with other parts. The level of expression being much stronger refers to a case wherein the expression of interest stronger by approximately ⅓ to ½ compared with expression of other parts. Specifically, when it is said that DNA "can be locally expressed in roots," this phrase means that although expression in leaves or stems may be observed, the expression in roots is more significantly remarkable than expressions in those parts.

Further, it is possible to introduce into a plant a promoter which enhances expression. As an example of the promoter, a non-translation region in (CMV 35S-up) upstream of the CMV 35S-P can be used.

Any terminator can be used as long as it functions in plant cells, for example, the terminator of a nopaline synthase gene can be used.

For DNA introduction into plants, chemical, physical and biological methods including electroporation, a method using a particle gun, and a method using Agrobacterium can be used to introduce DNA into a plant genome. Plant cells into which DNA is introduced, can be selected and redifferentiated by the use of a marker such as drug-resistant property of antibiotics and the like.

The plants usable in the present invention include any plant species as long as the redifferentiating method from cells, tissues, or organs is established and the gene introduction system is constructed. As preferable plant species, seed plants can be exemplified. Although the seed plants can be either herby plants or woody plants, herby plants are preferable due to easiness in cultivation, and examples thereof include tobacco, rice, and turf grass.

Since the protein of the present invention is secreted from the roots of the transformant plants prepared as above, the protein of the present invention can be obtained with few impurities by culturing the plants in a water culture solution and collecting the protein from the culture solution. The water culture solution is not particularly limited as long as it enables the transformant plants to grow therein and secrete the protein of the present invention, and Murashige & Skoog medium, for example, can be used. The transformant plant of the present invention is planted in the water culture solution and cultured at temperatures suitable for its growth. The time period necessary for sufficient secretion of phenoloxidase from the transformant plants varies depending on plant species to be used. Thus, while observing secretion condition of the enzyme, an appropriate culture period may be determined. However, usually the period is approximately one week. The protein of the invention secreted in the water culture solution can be collected by ordinary separation and purification methods for enzymes. For example, the culture solution containing phenoloxidase is centrifuged and further concentrated using an ultrafilter. Furthermore, a construction in which 6 histidine residues are linked with N- or C-terminus of phenoloxidase, is prepared and allowed to be expressed, and this can simplify the purification of the enzyme by purification resin of immobilized metal affinity chromatography. The thus obtained enzyme can be used in the fields of wastewater treatment, production of artificial lacquer paints, turbidity prevention of beverages, clinical analysis, etc.

Moreover, the protein of the present invention has a function to decompose and remove hazardous chemical substances as described above. Therefore, hazardous chemical substances can be decomposed and removed in the rooting zone sustainably and independently by cultivating the transformant plant of the present invention in environments contaminated with hazardous chemical substances. Further, it is possible to decompose and remove hazardous chemical substances by spraying the protein collected from the transformant plant of the present invention over the environments contaminated with hazardous chemical substances. As used herein, the term "hazardous chemical substances" means substances exhibiting toxicity or endocrine disruption to human bodies, and substances which can be decomposed or the toxicity of which can be reduced by the phenoloxidase, in particular laccase. To be more specific, examples thereof include chlorophenols, agricultural chemicals, polycyclic aromatic hydrocarbons, alkylphenol, aromatic hydrocarbons, and nitro compounds. Additionally, the term "environment" means, for example, soils, lakes, rivers and the like.

EXAMPLES

Example 1

Cloning of Laccase cDNA of *Coriolus versicolor*

In order to isolate cDNA encoding laccase, a nucleotide sequence of upstream and downstream regions of the region encoding laccase, that is 20 nucleotides from the initial codon and 22 nucleotides from the stop codon, was selected from nucleotide sequences of laccase genomes of *Coriolus versicolor* IFO 30340, which is registered under DDBJ accession No. D13372. Then, an oligonucleotide was chemically synthesized.

PCR was conducted using the above prepared oligonucleotide as primers and cDNA of *Coriolus versicolor* as a template. The reaction conditions for PCR were 25 cycles of 30 seconds at 94° C., 30 seconds at 55° C., and 90 seconds at 72° C. Pyrobest DNA polymerase (Takara Shuzo Co., Ltd.) was used for the reaction. A part of the reaction solution was subjected to 1.5% agarose gel electrophoresis for separation, and then amplified products of DNA having the expected size were observed. Fragments of the amplified products were excised from agarose and extracted, and then subjected to sequencing, thereby obtaining full-length cDNA indicated in SEQ ID NO:1. Further, an amino acid sequence corresponding thereto is shown in SEQ ID NO:2.

Example 2

Construction of a Vector and Introduction Thereof into a Plant

In order to obtain laccase cDNA into which a restriction enzyme site is introduced, primers were synthesized. Nucleotide sequences of respective primers are as follows.

```
                                          SEQ ID NO:3
    LfXb: 5'-ttgtttctagatgtcgaggtttcactctct-3'

SEQ ID NO:4
    LBa: 5'-aattggatccttactggtcgctcgggtcgagcg-3'
```

Using the above synthesized DNA as primers and laccase cDNA of SEQ ID NO:1 as a template, PCR was conducted by Pyrobest DNA polymerase. The reaction conditions for PCR were 30 cycles of 10 seconds at 98° C., 30 seconds at 60° C., 80 seconds at 72° C. A fragment in which Xba I and Bam HI restriction sites were added to full-length laccase cDNA (SEQ ID NO:1), was obtained by LfXb and LBa primers, and was inserted into pCR2.1. The nucleotide sequence was confirmed by sequencing.

The cDNA fragment amplified above was excised from pCR2.1 and inserted into Xba I, Bam HI sites of plasmid pBI221 comprising CMV 35S-P which enables strong expression particularly in plant roots. That plasmid was named as pfLac/pBI221.

Further, CMV 35S-up was inserted into Hind III and Pst I sites upstream of CMV 35S-P of the plasmid pfLac/pBI221, thereby attempting to enhance expression efficiency of the laccase gene. The obtained plasmid was named as pW35SfLac/pBI221.

The plasmid pW35SfLac/pBI221 was digested with Hind III and Bam HI, and a fragment containing CMV 35S-up, CMV 35S-P and laccase gene was inserted into Hind III, Bam HI sites of pBI121. That plasmid was named as pW35SfLac/pBI121 (FIG. 1).

*Agrobacterium tumefaciens* LBA4404 strain carrying pW35SfLac/pBI121 was used to introduce a secretory laccase gene into tobacco SR1 strain, thereby obtaining a transformant plant. In addition, a transformant plant of tobacco SR1 strain was obtained using *Agrobacterium tumefaciens* LBA4404 strain carrying pBI121, which was used as control. Southern analysis and PCR analysis were performed with whole DNA derived from each individual thereby confirming that each gene had been introduced into each of these transformant plants.

Example 3

Detection of Laccase Activity Secreted from Roots of Transformant Plants

Figure 2:
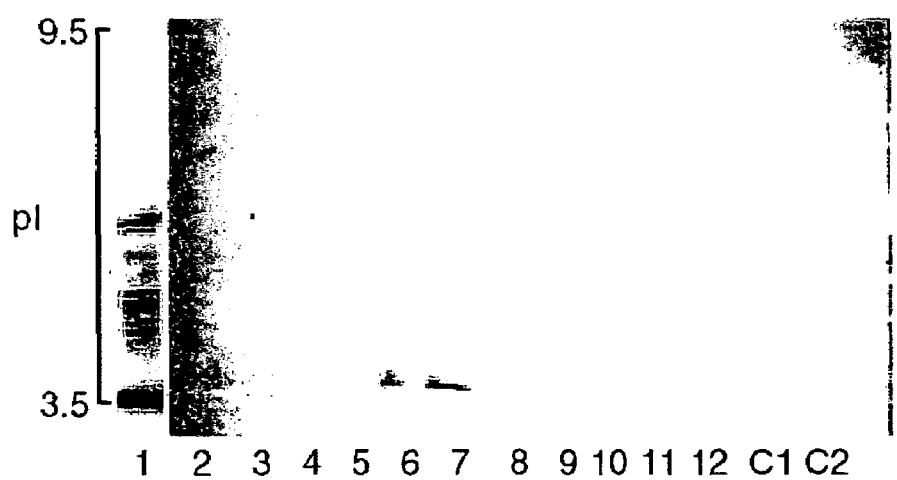
FIG. 2 shows the results obtained by conducting isoelectric focusing and activity staining on laccase secreted in culture solutions.

Murashige & Skoog medium containing one-fifth of the prescribed amount of saccharose was prepared as a water culture solution. The transformant plants of tobacco SRI strain, which had been prepared in Example 2 and grown to approximately 20 cm in length, were planted into the culture solution and cultivated at 28° C. After one-week of cultivation, 10 ml of the culture solution was collected, centrifuged at 12,000×g for 15 minutes, and concentrated to a concentration of 1/1,000 by a ultrafilter which eliminates molecules with a molecular weight of 10,000 or less. The protein concentration was then 10 µg/10 µl. This solution was developed by isoelectric focusing method and subjected to activity staining with 4-chloro-1-naphthol. The results are shown in FIG. 2. In the figure, numeral 1, numerals 2 to 12, and C1 to C2 represent the results for a crude enzyme solution of *Coriolus versicolor*, concentrates from the culture solution of transformant plants, and control plants (into which only pBI121 was introduced), respectively. As is clear from FIG. 2, a band around p13.5 which is an isoelectric point for laccase (numerals 2 to 11 in FIG. 2) was clearly observed only from the culture solution of the transformant plant into which a laccase gene was introduced. Further, no band was observed in the culture solution, prepared under the same conditions, for the control plants into which only pBI121 was introduced (C1 and C2 in FIG. 2).

According to the results stated above, it was clarified that the transformant plant having a laccase gene introduced thereinto secretes from its roots laccase having activity. Therefore, it is confirmed that it is possible to enable a transformant plant to secrete laccase from its roots by introducing laccase genes into herby plants or woody plants and allowing expression in the transformant plants.

All publications, patents and patent applications cited herein are incorporated by reference in their entirety.

EFFECT OF THE INVENTION

A plant of the present invention into which a phenoloxidase gene is introduced enables efficient and low-cost production of phenoloxidase. Further, hazardous chemical substances can be decomposed and removed by cultivating this plant in an environment contaminated with hazardous chemical substances.

What is claimed is:

1. A plant transformed with a DNA encoding a secretory laccase from *Coriolus versicolor*, wherein the DNA comprises the nucleotide sequence shown in SEQ ID NO: 1, and wherein the plant secretes the laccase from its roots.

2. The plant according to claim 1, wherein the plant is a seed plant.

3. A method of decomposing and/or removing hazardous chemical substances that can be decomposed or the toxicity of which can be reduced by laccases, comprising:
   cultivating the plant according to claim 1, in an environment contaminated with the hazardous chemical substances; and
   allowing the plant to decompose and/or remove the hazardous chemical substances.

4. The method of claim 3, wherein the plant is a seed plant.

5. A plant transformed with a DNA encoding a secretory laccase from *Coriolus versicolor*, wherein the DNA comprises the nucleotide sequence shown in SEQ ID NO:1, and wherein the DNA comprises a signal sequence sufficient to allow the laccase to be secreted from the roots of the plant.

6. The plant according to claim 5, wherein the signal sequence is a nucleotide sequence encoding amino acids 1–21 in SEQ ID NO:2.

7. The method of claim 3, wherein the hazardous chemical substances are diphenols or related compounds.

8. The method of claim 7, wherein the diphenols or related compounds are selected from the group consisting of: o-quinols, p-quinols, aminophenols and phenylenediamine.

9. A method of secreting a basidiomycete-derived laccase from the plant according to claim 1, comprising culturing said plant in a water solution; and secreting the laccase from the roots of the plant in the water culture solution.

* * * * *

SEQUENCE LISTING

<160> NUMBER OF SEQ ID NOS: 4

<210> SEQ ID NO 1
<211> LENGTH: 1563
<212> TYPE: DNA
<213> ORGANISM: Coriolus versicolor
<220> FEATURE:

```
<221> NAME/KEY: CDS
<222> LOCATION: (1)..(1563)

<400> SEQUENCE: 1 atg tcg agg ttt cac tct ctt ctc gct ttc gtc gtt gct tcc ctt acg      48
Met Ser Arg Phe His Ser Leu Leu Ala Phe Val Val Ala Ser Leu Thr
 1               5                  10                  15 gct gtg gcc cac gct ggt atc ggt ccc gtc gcc gac ctc acc atc acc      96
Ala Val Ala His Ala Gly Ile Gly Pro Val Ala Asp Leu Thr Ile Thr
             20                  25                  30 aac gca gcg gtc agc cct gat ggg ttt tct cgc cag gcc gtc gtc gtg     144
Asn Ala Ala Val Ser Pro Asp Gly Phe Ser Arg Gln Ala Val Val Val
         35                  40                  45 aac ggc ggc acc cct gga cct ctc atc acc ggt aac atg ggg gat cgc     192
Asn Gly Gly Thr Pro Gly Pro Leu Ile Thr Gly Asn Met Gly Asp Arg
     50                  55                  60 ttc cag ctc aat gtc atc gac aac ctc acc aac cac acg atg ctg aag     240
Phe Gln Leu Asn Val Ile Asp Asn Leu Thr Asn His Thr Met Leu Lys
 65                  70                  75                  80 agc acc agt att cac tgg cac ggt ttc ttc cag aag ggc acg aac tgg     288
Ser Thr Ser Ile His Trp His Gly Phe Phe Gln Lys Gly Thr Asn Trp
                 85                  90                  95 gcc gac ggt ccc gcc ttc atc aac cag tgc ccg atc tca tct ggt cac     336
Ala Asp Gly Pro Ala Phe Ile Asn Gln Cys Pro Ile Ser Ser Gly His
            100                 105                 110 tcg ttc ctg tac gac ttc cag gtt cct gac cag gct ggc acc ttc tgg     384
Ser Phe Leu Tyr Asp Phe Gln Val Pro Asp Gln Ala Gly Thr Phe Trp
        115                 120                 125 tac cac agt cac ttg tcc acg cag tac tgt gat ggt ctg agg ggt ccg     432
Tyr His Ser His Leu Ser Thr Gln Tyr Cys Asp Gly Leu Arg Gly Pro
    130                 135                 140 ttc gtt gtt tac gag ccg aat gag ccg gcc gcc gac ttg tac gac gtc     480
Phe Val Val Tyr Glu Pro Asn Glu Pro Ala Ala Asp Leu Tyr Asp Val
145                 150                 155                 160 gac aac gac gac act gtc att acc ctc gtg gat tgg tac cac gtc gcc     528
Asp Asn Asp Asp Thr Val Ile Thr Leu Val Asp Trp Tyr His Val Ala
                165                 170                 175 gcg aac gtg ggc cct gcc ttc cct ctc ggc gcc gat gcg acc ctc atc     576
Ala Asn Val Gly Pro Ala Phe Pro Leu Gly Ala Asp Ala Thr Leu Ile
            180                 185                 190 aat ggc aag gga cgc tcc ccc agc acg acc acc gcg gac ctc tct gtt     624
Asn Gly Lys Gly Arg Ser Pro Ser Thr Thr Thr Ala Asp Leu Ser Val
        195                 200                 205 atc agc gtc acc ccg ggt aaa cgg tac cgt ttc cgc ctg gtg tcc ctg     672
Ile Ser Val Thr Pro Gly Lys Arg Tyr Arg Phe Arg Leu Val Ser Leu
    210                 215                 220 tcg tgc gac ccc aac tac acg ttc agc atc gat ggt cac aac atg acg     720
Ser Cys Asp Pro Asn Tyr Thr Phe Ser Ile Asp Gly His Asn Met Thr
225                 230                 235                 240 atc atc gag acc gac tcg atc aac acg gcg ccc ctc gtg gtc gac tcc     768
Ile Ile Glu Thr Asp Ser Ile Asn Thr Ala Pro Leu Val Val Asp Ser
                245                 250                 255 att cag atc ttc gcc gcc cag cgt tac tcc ttc gtg ctc gag gcc aac     816
Ile Gln Ile Phe Ala Ala Gln Arg Tyr Ser Phe Val Leu Glu Ala Asn
            260                 265                 270 cag gcc gtc gac aac tac tgg att cgc gcc aac ccc aac ttc ggt aac     864
Gln Ala Val Asp Asn Tyr Trp Ile Arg Ala Asn Pro Asn Phe Gly Asn
        275                 280                 285 gtc ggg ttc acc ggc ggc atc aac tcg gct atc ctc cgc tac gat ggt     912
Val Gly Phe Thr Gly Gly Ile Asn Ser Ala Ile Leu Arg Tyr Asp Gly
    290                 295                 300
```

```
gcc gct gcc gtc gag ccc act acc acg cag acc act tcg acc gag ccg       960
Ala Ala Ala Val Glu Pro Thr Thr Thr Gln Thr Thr Ser Thr Glu Pro
305                 310                 315                 320 ctc aat gag gtc aac ctg cac ccg ttg gtt gcc acc gct gtt cct ggc      1008
Leu Asn Glu Val Asn Leu His Pro Leu Val Ala Thr Ala Val Pro Gly
                325                 330                 335 tct ccg ttt gcg ggt ggt gtc gac ctg gcc atc aac atg gcg ttc aac      1056
Ser Pro Phe Ala Gly Gly Val Asp Leu Ala Ile Asn Met Ala Phe Asn
            340                 345                 350 ttc aac ggc acc aac ttc ttc atc aac ggc gcg tct ttc acg ccc ccg      1104
Phe Asn Gly Thr Asn Phe Phe Ile Asn Gly Ala Ser Phe Thr Pro Pro
        355                 360                 365 acc gtg cct gtc ctc ctc cag atc atc agc ggc gcg cag aac gcg caa      1152
Thr Val Pro Val Leu Leu Gln Ile Ile Ser Gly Ala Gln Asn Ala Gln
370                 375                 380 gac ctc ctg ccc tct ggc agc gtc tac tcg ctc ccc tcg aac gcc gac      1200
Asp Leu Leu Pro Ser Gly Ser Val Tyr Ser Leu Pro Ser Asn Ala Asp
385                 390                 395                 400 atc gag atc tcg ttc ccc gcc acc gcc gcc gcc cct ggt gcg ccc cac      1248
Ile Glu Ile Ser Phe Pro Ala Thr Ala Ala Ala Pro Gly Ala Pro His
                405                 410                 415 ccc ttc cac ttg cac ggg cac gcg ttc ggc gtc gtc cgc agc gcc ggc      1296
Pro Phe His Leu His Gly His Ala Phe Gly Val Val Arg Ser Ala Gly
            420                 425                 430 agc aca gtc tac aac tac gac aac ccc atc ttc cgc gac gtc gtc agc      1344
Ser Thr Val Tyr Asn Tyr Asp Asn Pro Ile Phe Arg Asp Val Val Ser
        435                 440                 445 acg ggg acg cct gcg gcc ggt gac aac gtc acc atc cgc ttc cgc acc      1392
Thr Gly Thr Pro Ala Ala Gly Asp Asn Val Thr Ile Arg Phe Arg Thr
450                 455                 460 gac aac ccc ggc ccg tgg ttc ctc cat tgc cac atc gac ttc cac ctc      1440
Asp Asn Pro Gly Pro Trp Phe Leu His Cys His Ile Asp Phe His Leu
465                 470                 475                 480 gag ggc ggt ttc ggc gtc gtg ttg gcg gag gac atc gcc gac gtt gcg      1488
Glu Gly Gly Phe Gly Val Val Leu Ala Glu Asp Ile Ala Asp Val Ala
                485                 490                 495 tcg gcg aac ccc gtg ccc cag gcg tgg tcc gac ctc tgc ccg acc tac      1536
Ser Ala Asn Pro Val Pro Gln Ala Trp Ser Asp Leu Cys Pro Thr Tyr
            500                 505                 510 gat gcg ctc gac ccg agc gac cag taa                                   1563
Asp Ala Leu Asp Pro Ser Asp Gln
        515                 520

<210> SEQ ID NO 2
<211> LENGTH: 520
<212> TYPE: PRT
<213> ORGANISM: Coriolus versicolor

<400> SEQUENCE: 2

Met Ser Arg Phe His Ser Leu Leu Ala Phe Val Val Ala Ser Leu Thr
1               5                   10                  15

Ala Val Ala His Ala Gly Ile Gly Pro Val Ala Asp Leu Thr Ile Thr
            20                  25                  30

Asn Ala Ala Val Ser Pro Asp Gly Phe Ser Arg Gln Ala Val Val Val
        35                  40                  45

Asn Gly Gly Thr Pro Gly Pro Leu Ile Thr Gly Asn Met Gly Asp Arg
    50                  55                  60

Phe Gln Leu Asn Val Ile Asp Asn Leu Thr Asn His Thr Met Leu Lys
65                  70                  75                  80
```

-continued

```
Ser Thr Ser Ile His Trp His Gly Phe Phe Gln Lys Gly Thr Asn Trp
            85                  90                  95

Ala Asp Gly Pro Ala Phe Ile Asn Gln Cys Pro Ile Ser Ser Gly His
            100                 105                 110

Ser Phe Leu Tyr Asp Phe Gln Val Pro Asp Gln Ala Gly Thr Phe Trp
            115                 120                 125

Tyr His Ser His Leu Ser Thr Gln Tyr Cys Asp Gly Leu Arg Gly Pro
            130                 135                 140

Phe Val Val Tyr Glu Pro Asn Glu Pro Ala Ala Asp Leu Tyr Asp Val
145                 150                 155                 160

Asp Asn Asp Asp Thr Val Ile Thr Leu Val Asp Trp Tyr His Val Ala
            165                 170                 175

Ala Asn Val Gly Pro Ala Phe Pro Leu Gly Ala Asp Ala Thr Leu Ile
            180                 185                 190

Asn Gly Lys Gly Arg Ser Pro Ser Thr Thr Thr Ala Asp Leu Ser Val
            195                 200                 205

Ile Ser Val Thr Pro Gly Lys Arg Tyr Arg Phe Arg Leu Val Ser Leu
            210                 215                 220

Ser Cys Asp Pro Asn Tyr Thr Phe Ser Ile Asp Gly His Asn Met Thr
225                 230                 235                 240

Ile Ile Glu Thr Asp Ser Ile Asn Thr Ala Pro Leu Val Val Asp Ser
            245                 250                 255

Ile Gln Ile Phe Ala Ala Gln Arg Tyr Ser Phe Val Leu Glu Ala Asn
            260                 265                 270

Gln Ala Val Asp Asn Tyr Trp Ile Arg Ala Asn Pro Asn Phe Gly Asn
            275                 280                 285

Val Gly Phe Thr Gly Gly Ile Asn Ser Ala Ile Leu Arg Tyr Asp Gly
            290                 295                 300

Ala Ala Ala Val Glu Pro Thr Thr Thr Gln Thr Thr Ser Thr Glu Pro
305                 310                 315                 320

Leu Asn Glu Val Asn Leu His Pro Leu Val Ala Thr Ala Val Pro Gly
            325                 330                 335

Ser Pro Phe Ala Gly Gly Val Asp Leu Ala Ile Asn Met Ala Phe Asn
            340                 345                 350

Phe Asn Gly Thr Asn Phe Phe Ile Asn Gly Ala Ser Phe Thr Pro Pro
            355                 360                 365

Thr Val Pro Val Leu Leu Gln Ile Ile Ser Gly Ala Gln Asn Ala Gln
            370                 375                 380

Asp Leu Leu Pro Ser Gly Ser Val Tyr Ser Leu Pro Ser Asn Ala Asp
385                 390                 395                 400

Ile Glu Ile Ser Phe Pro Ala Thr Ala Ala Pro Gly Ala Pro His
            405                 410                 415

Pro Phe His Leu His Gly His Ala Phe Gly Val Val Arg Ser Ala Gly
            420                 425                 430

Ser Thr Val Tyr Asn Tyr Asp Asn Pro Ile Phe Arg Asp Val Val Ser
            435                 440                 445

Thr Gly Thr Pro Ala Ala Gly Asp Asn Val Thr Ile Arg Phe Arg Thr
            450                 455                 460

Asp Asn Pro Gly Pro Trp Phe Leu His Cys His Ile Asp Phe His Leu
465                 470                 475                 480

Glu Gly Gly Phe Gly Val Val Leu Ala Glu Asp Ile Ala Asp Val Ala
            485                 490                 495
```

```
Ser Ala Asn Pro Val Pro Gln Ala Trp Ser Asp Leu Cys Pro Thr Tyr
            500                 505                 510

Asp Ala Leu Asp Pro Ser Asp Gln
        515                 520

<210> SEQ ID NO 3
<211> LENGTH: 30
<212> TYPE: DNA
<213> ORGANISM: Artificial Sequence
<220> FEATURE:
<223> OTHER INFORMATION: Primer LfXb

<400> SEQUENCE: 3
ttgtttctag atgtcgaggt ttcactctct                                30

<210> SEQ ID NO 4
<211> LENGTH: 33
<212> TYPE: DNA
<213> ORGANISM: Artificial Sequence
<220> FEATURE:
<223> OTHER INFORMATION: Primer LBa

<400> SEQUENCE: 4
aattggatcc ttactggtcg ctcgggtcga gcg                            33
```